US007214538B2

(12) United States Patent
Benco et al.

(10) Patent No.: US 7,214,538 B2
(45) Date of Patent: May 8, 2007

(54) DEVICE AND METHOD FOR THE DETERMINATION OF LITHIUM ION CONCENTRATION IN A BIOLOGICAL FLUID

(75) Inventors: John S. Benco, Holliston, MA (US); Hubert A. Nienaber, Worcester, MA (US); W. Grant McGimpsey, West Boylston, MA (US)

(73) Assignees: Worcester Polytechnic Institute, Worcester, MA (US); Bayer Health Care, LLC., East Walpole, MA (US)

( * ) Notice: Subject to any disclaimer, the term of this patent is extended or adjusted under 35 U.S.C. 154(b) by 0 days.

(21) Appl. No.: 10/776,063

(22) Filed: Feb. 11, 2004

(65) Prior Publication Data

US 2004/0161854 A1 Aug. 19, 2004

Related U.S. Application Data

(60) Provisional application No. 60/446,525, filed on Feb. 12, 2003.

(51) Int. Cl.
*G01N 33/20* (2006.01)
*G01N 21/64* (2006.01)
*G01N 21/01* (2006.01)
*C07D 291/00* (2006.01)

(52) U.S. Cl. .................. 436/79; 422/82.05; 422/82.06; 422/82.07; 422/82.08; 422/82.09; 436/73; 436/166; 436/169; 436/172; 540/468; 540/469; 540/470; 540/471; 549/346; 549/347; 549/348

(58) Field of Classification Search .. 422/82.05–82.09; 436/73, 79, 164, 166, 169, 172; 540/467–471; 549/346–348

See application file for complete search history.

(56) References Cited

U.S. PATENT DOCUMENTS 4,659,815 A * 4/1987 Pacey et al. ................ 540/467
5,599,913 A 2/1997 Harris et al. ................ 534/856

(Continued)

FOREIGN PATENT DOCUMENTS

WO 97/39337 * 10/1997

(Continued)

OTHER PUBLICATIONS de Silva, A. P. et al, Journal of the Chemical Society, Chemical Communications 1986, 1709-1710.*

(Continued)

*Primary Examiner*—Arlen Soderquist
(74) *Attorney, Agent, or Firm*—Edwards Angell Palmer & Dodge, LLP.

(57) ABSTRACT

The present invention relates to a novel device and method for the detection of lithium ions in a biological fluid. In a preferred embodiment, the present invention provides a novel compound and a optical sensor which incorporates said compound for the detection of lithium ions. Additionally, the present invention provides a method of detecting lithium ions which comprises placing the novel optical sensor into communication with a biological fluid. Once the novel compound of the present invention encounters a lithium ion(s), a fluorescence is generated, the intensity of which is measured and allows for the determination of lithium ion concentration. The present invention provides a medical professional with the ability to selectively determine lithium ion concentration in a biological fluid thereby facilitating the treatment of various diseases, such as manic-depressive illness.

29 Claims, 2 Drawing Sheets

U.S. PATENT DOCUMENTS

| | | | | |
|---|---|---|---|---|
| 5,641,684 | A | * | 6/1997 | Moore et al. .................. 436/73 |
| 5,926,687 | A | * | 7/1999 | Dozol et al. .................... 423/8 |
| 6,417,005 | B1 | * | 7/2002 | Barnard et al. ............... 436/73 |
| 6,660,526 | B2 | * | 12/2003 | Benco et al. .................. 436/79 |
| 2003/0119195 | A1 | | 6/2003 | Benco et al. .................. 436/79 |
| 2003/0159948 | A1 | | 8/2003 | Benco et al. ............... 205/789 |

OTHER PUBLICATIONS

Kim, J. S. et al, Journal of Organic Chemistry 2000, 65, 2386-2392.*

Kim, J. S. et al, Journal of Organic Chemistry 2002, 67, 2348-2351.*

Sabbatini, N. et al, Inorganica Chimica Acta 1996, 252, 19-24, no month.*

Chen, Y. et al, Synthetic Communications 1999, 29, 705-711, no month.*

Kim, J. S. et al, Journal of Organic Chemistry 2000, 65, 2386-2392, no month.*

Marchand, A. P. et al, Tetrahedron 2000, 56, 3121-3126, no month.*

Chen, Y. et al, Tetrahedron Letters 2000, 41, 4815-4818, no month.*

Sienko M. J. et al, "Chemical Principles and Properties" 1974, pp. 769-770, McGraw-Hill , Inc.: New York, New York.*

Yang, F. et al, Supramolecular Chemistry 2001, 12, 445-450.*

Benco, J. S. et al, Sensors and Actuators B 2002, 85, 126-130.*

Benco, J. S. et al, Journal of Photochemistry and Photobiology, A: Chemistry 2004, 162, 289-296.*

Arduini et al., "Calix[4]arenes Blocked in a Rigid Cone Conformation by Selective Functionalization at the Lower Rim", J. Org. Chem., 1995, v 60, p. 1454-1457.

Benco et al., "A Fluoroionophore for Detection of Potassium ions: 9-anthryl-substituted Azacrown Ether Covalently Linked to a 1,3-alternate Calix[4]arene", J. of Photochemistry and Photobiology A: Chemistry, 2002, v 152 p. 33-40.

Krause et al., "Emulsion-Based Fluorosensors for Potassium Featuring Improved Stability and Signal Change", Anal. Chem., 1999, v 71, p. 5304-5308.

McCarrick et al., "Chromogenic Ligands for Lithium Based on Calix[4]arene Tetraesters Bearing Nitrophenol Residues", J. Chem. Soc. Perkin Trans. 2, 1993, p. 1963-1968.

Prasanna de Silva et al., "Signaling Recognition Events with Fluorescent Sensors and Switches", Chem. Rev., 1997, v 97, p. 1515-1566.

Rehm et al., "Kinetics of Fluorescence Quenching by Electron and H-Atom Transfer", Israel Journal of Chemistry, 1979, v 8, p. 259-271.

Valeur, Bernard, "Fluorescent Molecular Sensors of Ions and Molecules", Molecular Fluorescence: Principles and Applications, 2001, p. 273-314.

Weller, Albert, "Photoinduced Electron Transfer in Solution: Exciplex and Radical Ion Pair Formation Free Enthalpies and their Solvent Dependence", 1982, p. 93-98.

* cited by examiner

DEVICE AND METHOD FOR THE DETERMINATION OF LITHIUM ION CONCENTRATION IN A BIOLOGICAL FLUID

RELATED APPLICATION(S)

This application claims the benefit of U.S. Provisional Application No. 60/446,525, filed on Feb. 12, 2003. The entire teachings of the above application is incorporated herein by reference.

FIELD OF THE INVENTION

The invention relates generally to the detection of ions by ion selective compounds. More specifically, the invention relates to the detection of lithium ions in a biological fluid wherein such detection may facilitate the treatment of manic depressive illness.

BACKGROUND

Manic depressive illness, known in medical communities as bipolar illness, is the most distinct and dramatic of the depressive or affective disorders. Unlike major depression, which occurs at any age, manic-depressive illness generally strikes before the age of 30. Almost 2 million Americans suffer from bipolar illness.

The distinction between bipolar illness and other depressive disorders is that patients swing from depression to mania, generally with periods of normal moods in between the two extremes. Some patients, however, cycle from mania to depression and back within a few days and without a period of normal mood. People with this condition are called rapid cyclers.

Though manic-depressive disorder can become disabling, it also is among the most treatable of the mental illnesses. The combination of psychotherapy and medications returns the vast majority of manic-depressive patients to functioning lives.

The most common medication, lithium carbonate, successfully reduces the number and intensity of manic episodes for a majority of those who take the medication. Twenty percent become completely free of symptoms. Those who respond to lithium best are patients who have a family history of depressive illness and who have periods of relatively normal mood between their manic depressive phases.

Very effective in treating the manic phase, lithium also appears to prevent repeated episodes of depression. One theory for this is that in controlling the mania, lithium helps prevent the swing into depression.

Lithium works by bringing various neurotransmitters in the brain into balance. Scientists think the medication may affect the way or the speed at which the brain cells break down the neurotransmitters that are thought to control moods.

However, like all medications, lithium can have side effects and must be very closely monitored by a psychiatrist. The doctor should measure the level of lithium in the patient's blood as well as how well the patient's kidneys and thyroid gland are working. Among the side effects are weight gain, excessive thirst and urination, stomach and intestinal irritation, hand tremors, and muscular weakness. More serious side effects are hypothyroidism, kidney damage, confusion, delirium, serious seizures, coma and, in patients who are not closely monitored by a physician, even death.

The amount of lithium needed to treat or prevent manic and depressive symptoms effectively differs greatly from one patient to another. The doctor determines how much lithium a patient needs by taking a sample of blood from time to time. The blood is analyzed to determine how much lithium is present. Testing for the lithium blood level is a vital part of treatment with lithium. It aids the doctor in selecting and maintaining the most effective dose. Just as important, lithium blood levels assure the doctor that a patient is not taking a toxic dose-that is, a poisonous dose. Lithium is an unusual drug because the amount needed to be effective is only slightly less than the amount that is toxic. For that reason, patients must be very careful not to take more lithium than prescribed. Lithium levels in the blood can change even when the patient takes the same dose every day: The concentration of lithium can increase when a person becomes ill with another medical condition, especially influenza or other illnesses that result in fever or changes in diet and loss of body fluids. Surgery, strenuous exercise, and crash diets are other circumstances that can lead to dangerously increased lithium levels in the blood. The doctor should be informed of illness or changes in eating habits, and a regular blood testing schedule should be set up and followed rigorously. If a patient stops taking lithium for only one day, the blood level of the drug falls to half that needed for effective therapy. A forgotten dose should not, however, be taken with the regular dose the next day, because it could raise the lithium level too much. Furthermore, the lower lithium level that results from missing one dose is unlikely to jeopardize therapeutic response. Because the blood level of lithium rises rapidly for a few hours after swallowing a lithium pill and then slowly levels off, having a blood test right after taking the drug can mislead the doctor into thinking that the dose is too high. To gauge the average blood level accurately, it is important to have blood drawn about 12 hours after the last dose of lithium. Otherwise, the results will be misleading and possibly dangerous. Most patients take their nighttime dose of lithium and then come to the doctor's office the next morning to have a blood test before taking their first dose for the day. Some patients are able to take their full daily dose at bedtime and do not have to worry about the morning dose when getting a blood level.

Lithium is excreted from the body almost entirely by the kidneys. If, for some reason, the kidneys are unable to get rid of the proper amount of lithium, the drug may accumulate to dangerous levels in the body. The excretion of lithium in the kidneys is closely linked to that of sodium. The less sodium, or salt, in the body, the less lithium is excreted, and the greater chance of lithium buildup to toxic levels. Diuretics cause the kidneys to excrete sodium; as a result, lithium levels rise. The reason that many illnesses can increase lithium levels is that increased sweating, fever, a low salt diet, vomiting, and diarrhea all result in less sodium present in the body, thus producing higher levels. Lithium should not be taken by patients with severely impaired kidney function. Patients with heart disease and others who have a significant change in sodium in their diet or periodic episodes of heavy sweating should be especially careful to have their lithium blood levels monitored regularly.

As explained above, lithium concentration in the blood needs to be carefully monitored. A novel, accurate and efficient optical sensor allowing a medical professional to monitor and regulate such lithium levels by accurately distinguishing between potassium, sodium and lithium ions would be an excellent tool for the treatment of diseases such as manic depressive illness.

As such, there is a need in the art for an efficient and reliable device and method capable of measuring lithium ion concentration of a biological fluid.

SUMMARY OF THE INVENTION

The present invention relates to a new molecule suitable for the optical detection of lithium ions. The molecule can be termed a fluoro or chromoionophore and is based upon the covalent linkage of a fluoro or chromophore to an aza-crown-3 calix[4]arene ionophore. The molecule of the present invention has the following structure:

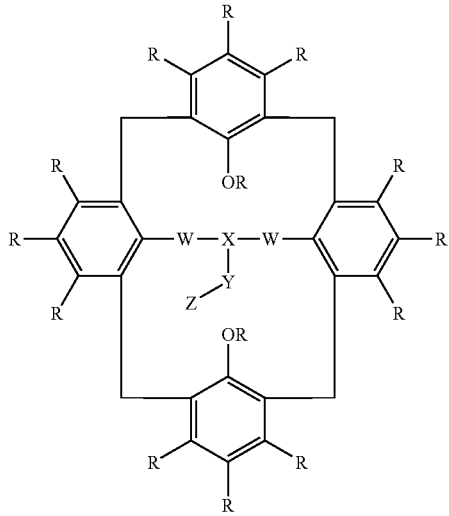

where (a) R is hydrogen, a saturated or unsaturated alkyl or aryl group, an ether, a carboxylic acid or ester group, or an alkyl or aryl group containing nitrogen or sulfur, independently or in combination; (b) W is —O(CH$_2$)$_2$—; (c) X is nitrogen, substituted or unsubstituted aryl, with or without heteroatoms, such as nitrogen, sulfur, oxygen, or saturated and unsaturated alkyl, (d) Y is saturated or unsaturated alkyl or aryl, ether, carboxylic containing, nitrogen or sulfur independently or in combination and (e) Z is an unsubstituted or substituted aryl group or groups (a fluorophore or chromophore), such that the presence of Z in the compound allows for the optical detection either through modulation of absorption and/or fluorescence.

In a preferred embodiment of the present invention, the molecule has the following structure:

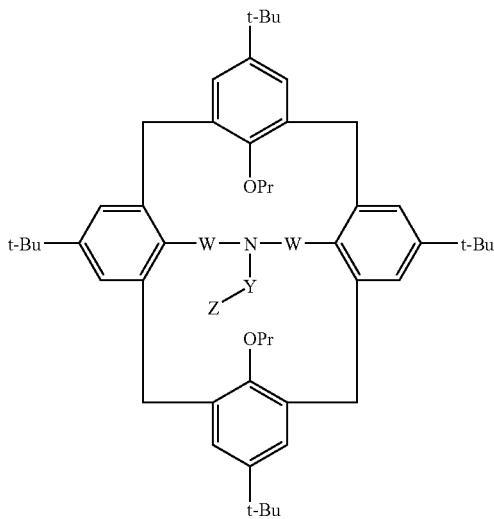

where W is —O(CH$_2$)$_2$, Y is —CH$_2$ and Z, the fluorophore, is anthracene.

The present invention further provides an optical sensor for the detection of lithium ions, comprising a support structure engaging the compound of the general structure shown above.

In one embodiment, the present invention provides an ion selective electrode comprising the above-identified novel compound.

Additionally, the present invention provides a method of detecting lithium ions comprising providing an optical sensor wherein the optical sensor includes the novel compound described above. Next, the optical sensor is placed into a biological fluid. Further, the optical sensor of the present invention produces a signal once the sensor encounters a lithium ion(s). Preferably, the sensor produces a measurable fluorescence when the novel compound engages a lithium ion(s). Finally, the fluorescence is measured and the lithium ion concentration may be determined.

The present invention provides an efficient and accurate device and method of determining lithium ion concentration of a biological fluid wherein the biological fluid comprises lithium, potassium and sodium ions.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

Figure 1:
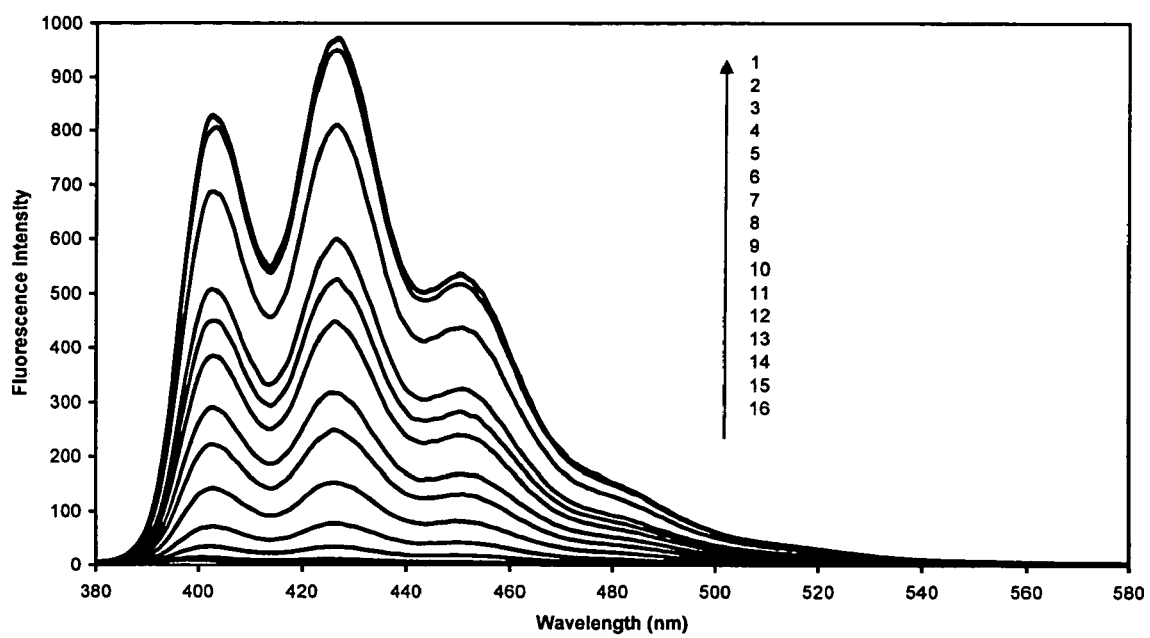
FIG. 1 shows a fluorescence emission spectrum of the title compound as a function of increasing lithium concentration.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

The calixarenes are a class of cyclooligomers formed via a phenol-formaldehyde condensation. They exist in a 'cup' like shape with a defined upper and lower rim and a central annulus. Their rigid conformation enables calixarenes to act as host molecules as a result of their preformed cavities. By functionally modifying either the upper and/or lower rims it is possible to prepare various derivatives with differing selectivities for various guest ions and small molecules. Calixarenes lend themselves well to many applications because of their multiplicity of options for such structural elaboration.

The molecule of the present invention has the following general structure:

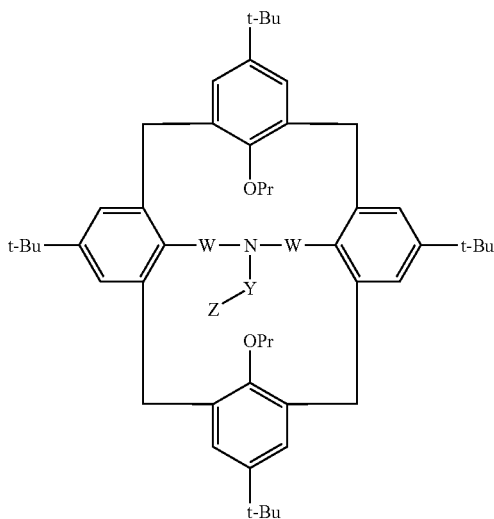

where (a) R is hydrogen, a saturated or unsaturated alkyl or aryl group, an ether, a carboxylic acid or ester group, or an alkyl or aryl group containing nitrogen or sulfur, independently or in combination; (b) W is —O(CH$_2$)$_2$—; (c) X is nitrogen, substituted or unsubstituted aryl, with or without heteroatoms, such as nitrogen, sulfur, oxygen, or saturated and unsaturated alkyl, (d) Y is saturated or unsaturated alkyl or aryl, ether, carboxylic containing, nitrogen or sulfur independently or in combination and (e) Z is an unsubstituted or substituted aryl group or groups (a fluorophore or chromophore), such that the presence of Z in the compound allows for the optical detection either through modulation of absorption and/or fluorescence.

In a preferred embodiment of the present invention, the molecule has the following structure:

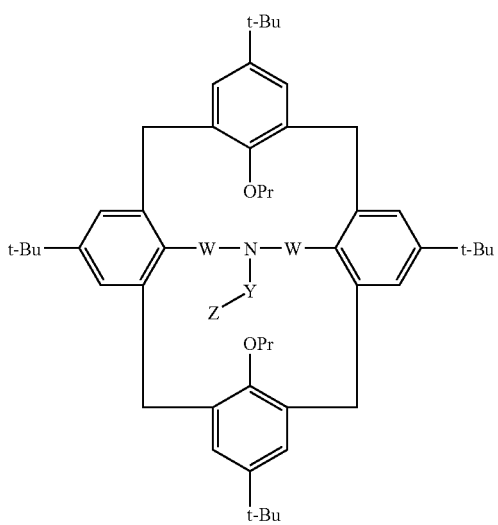

where W is —O(CH$_2$)$_2$—, Y is —CH$_2$ and Z is the fluorophore.

The molecule of the present invention incorporates three components, namely a fluorophore, a host-guest site (ionophore) and a spacer module. In the preferred embodiment, the novel molecule of the present invention operates based upon the photoinduced electron transfer ("PET") mechanism. The PET mechanism is particularly attractive since it is known to give the greatest signal to noise ratios.

Signal transduction in the fluoroionophore of the present invention is modulated by the PET mechanism, well known to those of skill in the art. Specifically, ion complexation within the aza-crown-3 calix[4]arene binding site suppresses electron transfer to the excited fluorophore and thereby increases the fluorescence intensity. The increase of fluorescence can be related linearly to the measured ion concentration or activity. An extensive review of the subject matter has been given by de Silva A et al., "Signaling Recognition Events with Fluorescent Sensors and Switches", *Chem. Rev.* 97: 1515–1556 (1997).

The novel compound of the present invention comprises an aza crown calixarene. By utilizing an aza crown calixarene, a convenient attachment site for a fluorophore or chromophore is available via the secondary amine. Covalent attachment can be accomplished by any one of several well-known methods.

In a preferred embodiment of the present invention, the fluorophore is anthracene. In alternative embodiments, other chromophores or fluorophores can be attached to the aza-crown-3-calix[4]arene ionophoric moiety such that the signaling mechanism could be tailored to specific needs. In one embodiment of the present invention, the novel molecule may operate on any number of various charge transfer effects such as nitrophenols, azophenols or donor-acceptors such as pyrene-phenylnitro or potential sensitive dyes or excimer systems or well-known pH sensitive molecules such as fluorescein.

In one embodiment of the present invention, Z may be any fluorophore or chromophore that satisfy the needed application. In a preferred embodiment of the present invention, Z is a fluorophore that allow for a negative, thermo-neutral or slightly positive free energy value to be obtained from the Rehm-Weller equation (Rehm D & Weller A, *Isr. J. Chem* 8: 259–271 (1970)):

$$\Delta G° = E_{ox}°(\text{donor}) - E_{red}°(\text{acceptor}) - E_{o,o} + C$$

where $E_{ox}°(\text{donor})$ is the oxidation potential of the donor group (i.e., nitrogen), $E_{red}°(\text{acceptor})$ is the reduction potential of the acceptor group (i.e., fluorophore), $E_{o,o}$ is the singlet state energy of the fluorophore and C is a Coulombic term relating to the energy of separated ions and which can be neglected in aqueous solutions (Weller AZ, *Phys. Chem. Neu. Folg.* 133:93 (1982)).

An acceptable "slightly positive free energy value" can be in the range of about 0 kcal/mol to about 10 kcal/mol. Those skilled in the art will recognize that various free energy values are within the spirit and scope of the present invention. A preferred free energy value can be determined by one of skill in the art depending on the electron donor/fluorophore pair chosen and the temperature.

Fluorophores can be obtained from commercial sources. For example, fluorophores can be obtained from Molecular Probes, Inc. (Eugene, Oreg., USA) or Amersham Pharmacia Biotech (Buckinghamshire, England, UK).

The following EXAMPLES are presented in order to more fully illustrate the preferred embodiments of the invention. These EXAMPLES should in no way be construed as limiting the scope of the invention, as defined by the appended claims.

EXAMPLES

Synthesis of Preferred Embodiment $^1$H- and $^{13}$C-NMR spectra were recorded with a Bruker Avance 400 in CDCl$_3$. All solvents and reagents were used as supplied from Aldrich (http://www.sirgmaaldrich.com) unless stated otherwise. 4-tert-Butylcalix[4]arene was purchased from Acros (http://www.fisher.co.uk/acros/).

Preparation of N-(9-methyl-anthracene)-25,27-Bis(1-propyloxy)-4-tert-Butylcalix[4]arene-Azacrown-3: Preferred embodiment A mixture of 200 mg (0.25 mmol) 25,27-Bis(1-propyloxy)-4-tert.-Butylcalix[4]arene-Azacrown-3, 85 mg (0.37 mmol) 9-(Chloromethyl)anthracene, 75 mg (0.75 mmol) Triethylamine and 17 mg (0.1 mmol) KI in 80 ml of dry Dioxane was refluxed for 48 h under nitrogen and protected from light. The solvent was removed in vacuo and 50 ml 2N KOH and 50 ml CH$_2$Cl$_2$ were added and the phases were separated. The aqueous phase was extracted two times with 30 ml CH$_2$Cl$_2$, the organic phases were combined, dried with Na$_2$SO$_4$ and the solvent removed in vacuo. 80 mg of the crude product was purified on prep. TLC using CH$_2$Cl$_2$/Et$_3$N (50/1)(R$_f$0.25). This faction was almost pure and yielded after recrystallisation from Methanol/CH$_2$Cl$_2$ (4:1) 26 mg (31%) of the pure N-(9-methyl-anthracene)-25,27-Bis(1-proploxy) -4-tert.-Butylcalix[4]arene-Azacrown-3 as slightly yellow crystals. $^1$H NMR (CDCl$_3$); δ0.55 (t, 6H, OCH$_2$CH$_2$CH$_3$), δ0.70 (m, 4H, OCH$_2$CH$_2$CH$_3$), δ1.10 (s, 18H, C(CH$_3$)$_3$), δ1.27 (s, 18H, C(CH$_3$)$_3$), δ1.70 (m, 4H, OCH$_2$CH$_2$N), δ3.15 (m, 4H, OCH$_2$CH$_2$CH$_3$), δ3.52 (m, 4H, OCH$_2$CH$_2$N), δ4.01 (m, 8H, Ar—CH$_2$—Ar), δ4.06 (s, 2H, N—CH$_2$—Ar), δ7.00 (s, 4H, ArH meta), δ7.05 (s, 4H, ArH meta), δ7.40 (m, 4H, Anthr.-H), δ7.92 (m, 2H, Anthr.-H), δ8.20 (m,2H, Anthr.-H), δ8.31 (s, 1H, Anthr.-H), $^{13}$C NMR (CDCl$_3$); δ10.16, δ21.95, δ31.80, δ31.94, δ34.22, δ34.32, δ40.22, δ49.71, δ51.42, δ70.18, δ74.49, δ125.07, δ125.58, δ125.67, δ126.58, δ126.85, δ129.14, δ131.46, δ131.71, δ131.84, δ132.23, δ134.35, δ143.61, δ145.34, δ155.50, δ155.88.

Preparation of Dipropyl-4-tert-Butylcalix[4]arene

In a 500 ml round bottom flask 6.489 g 4-tert-Butylcalix[4]arene (10.00 mmol), 4.10 g 1-Iodopropane (24.1 mmol=2.4 equiv.) and 4.14 g (30 mmol) K$_2$CO$_3$ were suspended in 300 ml dry Acetonitrile and boiled under reflux for 24 hours. The solvent was removed in vacuo and 50 ml 2N HCl and 50 ml CH$_2$Cl$_2$ were added and the phases were separated. The aqueous phase was extracted two times with 30 ml CH$_2$Cl$_2$, the organic phases were combined dried with Na$_2$SO$_4$ and the solvent removed in vacuo. The crude product was recrystallized from Methanol/CH$_2$Cl$_2$ (5:1) and gave 5.57 g (76%) of Dipropyl-4-tert-Butylcalix[4]arene as white crystals. $^1$H NMR (CDCl$_3$); δ1.03 (s, 18 H, C(CH$_3$)$_3$), δ1.26 (s, 24 H, C(CH$_3$)$_3$ and OCH$_2$CH$_2$CH$_3$), δ2.03 (m, 4H, OCH$_2$CH$_2$CH$_3$)$_3$), δ3.31 (d, 4H, Ar—CH$_2$—Ar), δ3.95 (tm 4H, OCH$_2$CH$_2$CH$_3$), δ4.30 (d, 4H, Ar—CH$_2$—Ar), δ6.88 (s, 4H, ArHmeta), δ6.93 (s, 4H, ArH meta), δ8.00 (s, 2H, OH). $^{13}$C NMR (CDCl$_3$); δ11.32, δ23.86, δ31.52, δ32.12, δ32.30, δ34.21, δ34.41, δ78.50, δ125.48, δ125.90, δ128.12, δ133.34, δ141.64, δ147.09, δ150.36, δ151.25.

Preparation of Dipropyl-(Di-2-chloroethoxy)-4-tert-Butylcalixr[4]arene

To a solution of 7.329 g (10 mmol) Dipropyl-4-tert-Butylcalix[4]arene in 300 ml dry Acetonitrile, 9.39 g (40 mmol) 2-Chloroethyl-p-toluenesulfonate and 9.77 g (30 mmol) CS$_2$CO$_3$ were added and the mixture was refluxed under nitrogen for 24 h. The solvent was removed in vacuo and 50 ml 2N HCl and 50 ml CH$_2$Cl$_2$ were added and the phases were separated. The aqueous phase was extracted two times with 30 ml CH$_2$Cl$_2$, the organic phases were combined dried with Na$_2$SO$_4$ and the solvent removed in vacuo. The crude product was recrystallized from Methanol/ CH$_2$Cl$_2$ (3:1) and gave 4.89 g (57%) of Dipropyl-(Di-2-chloroethoxy) 4-tert-Butylcalix [4]arene as white crystals. $^1$H NMR (CDCl$_3$); δ0.55 (t, 6H, OCH$_2$CH$_2$CH$_3$), δ0.93 (m, 4H, OCH$_2$CH$_2$CH$_3$), δ1.26 (s, 18H, C(CH$_3$)$_3$), δ1.31 (s,18H, C(CH$_3$)$_3$, δ2,60 (m, 4H, OCH$_2$CH$_2$Cl), δ3.30 (t, 4H, OCH$_2$CH$_2$CH$_3$), δ3.52 (m, 4H, OCH$_2$CH$_2$Cl), δ3.83 (m, 8H, Ar—CH$_2$—Ar), δ6.95 (s, 4H, ArH meta), δ6.97 (s, 4H, ArH meta). $^{13}$C NMR (CDCl$_3$); δ10.08, δ22.35, δ31.51, δ31.67, δ33.95, δ34.02, δ39.06, δ40.09, δ68.80, δ71.29, δ125.22, δ125.62, δ132.68, δ133.01, δ144.51, δ144.61, δ153.34, δ154.97.

Preparation of N-Tosyl 25,27-Bis(1-propyloxy)-4-tert-Butylcalix[4]arene Azacrown-3

A solution of 2.58 g (3 mmol) 25,27-Bis(1-propyloxy)-26,28-bis(2-chloroethoxy)-4-tert -Butylcalix[4]arene, 0.513 g (3 mmol) p-Toluenesulfonamide, 4.89 g (15 mmol) Cs$_2$CO$_3$ and 0.17 g (1 mmol)KI in 150 ml dry DMF was heated at reflux under Nitrogen for 24 h. The solvent was removed in vacuo and 50 ml 2N HCl and 50 ml CH$_2$Cl$_2$ were added and the phases were separated. The aqueous phase was extracted two times with 30 ml CH$_2$Cl$_2$, the organic phases were combined dried with Na$_2$SO$_4$ and the solvent was removed in vacuo. The crude compound was recrystallized from Methanol/CH$_2$Cl$_2$ (4:1) and gave 1.45 g (51%) of N-Tosyl 25,27-Bis(1-propyloxy)-4-tert.-Butylcalix[4]arene Azacrown-3 as white crystals.

$^1$H NMR (CDCl$_3$); δ0.56 (t, 6H, OCH$_2$CH$_2$CH$_3$), δ0.68 (m,4H,OCH$_2$CH$_2$CH$_3$), δ1.11 (s,18 H, C(CH$_3$)$_3$), δ1.26 (s,18 H, C(CH$_3$)$_3$), δ2.20 (m, 4H, OCH$_2$CH$_2$N), δ2.39 (s, 3H, Ar—CH$_3$), δ3.14 (m, 4H, OCH$_2$CH$_2$CH$_3$), δ3.36 (m, 4H, OCH$_2$CH$_2$N), δ3.94 (m, 8H, Ar—CH$_2$—Ar), δ7.04 (s, 8H, ArH meta), δ7.19 (d, 2H, ArHortho), δ7.48 (d, 2H, Ar H meta), $^{13}$C NMR (CDCl$_3$); δ10.09, δ21.87, δ31.71, δ31.93, δ34.25, δ40.06, δ50.75, δ72.48, δ74.16, δ126.52, δ126.82, δ127.24, δ129.96, δ132.49, δ134.21, δ136.98, δ143.08, δ144.05, δ145.66, δ155.02, δ155.62.

Preparation of 25,27-Bis(1-propyloxy)-4-tert-Butylcalix[4]arene Azacrown-3

To a solution of 1.2 g (1.25 mmol) N-Tosyl 25,27-Bis(1-propyloxy)-4-tert.-Butylcalix [4]arene Azacrown-3 in 80 ml dry THF was added 1 g potassium carefully under nitrogen. The mixture was heated to reflux for 24 h, at which temperature the potassium was molten, and then allowed to cool to room temperature. The main excess of potassium was removed and the rest was carefully hydrolysed with water. The solvent was removed in vacuo and 50 ml 1N KOH and 50 ml $CH_2Cl_2$ were added and the phases were separated. The aqueous phase was extracted two times with 30 ml $CH_2Cl_2$, the organic phases were combined dried with $Na_2SO_4$ and the solvent removed in vacou. The crude compound was recrystallized from Methanol/$CH_2Cl_2$ (4:1) and gave 0.82 (82%) of 25,27-Bis(1-propyloxy)-4-tert.-Butylcalix[4]arene Azacrown-3 as white crystals. $^1H$ NMR ($CDCl_3$); s0.55 (t, 6H, $OCH_2CH_2C\underline{H}_3$), δ0.81 (m,4H, $OCH_2C\underline{H}_2CH_3$), δ1.23 (s, 18H, $C(C\underline{H}_3)_3$), δ1.27 (s, 18H, $C(C\underline{H}_3)_3$), δ1.89 (m, 4H, $OCH_2C\underline{H}_2N$), δ3.10 (m, 4H, $OC\underline{H}_2CH_2CH_3$), δ3.26 (m, 4H, $OC\underline{H}_2CH_2N$), δ3.95 (m, 8H, Ar—$CH_2$—Ar), δ6.95 (s, 4H, Ar$\underline{H}$ meta), δ6.99 (s, 4H, Ar $\underline{H}$ meta) $^{13}C$ NMR ($CDCl_3$); δ10.00, δ22.06, δ31.52, δ31.59, δ33.86, δ34.04, δ39.79, δ47.81, δ68.06, δ72.72, δ125.93, δ125.98, δ132.44, δ133.13, δ143.87, δ144.94, δ153.98, δ155.96.

The novel molecule of the present invention was tested to show the molecule's ability to detect the presence of lithium ions. Testing of the compound was performed in solution using dichloromethane and tetrahydrofuran (75:25) at a concentration of 2 μM. A proton scavenger, benzyltrimethylammonium hydroxide was added (6 μM). Fluorescence spectra were recorder on a Perkin Elmer LS50B at an excitation wavelength of 355 nm. Alkali metals were added as the hexafluorphosphate salts.

FIG. 1 shows the fluorescence emission spectrum of the title compound as a function of increasing lithium concentration, where 1–16 are 0, 0.5, 1.0, 1.5, 2.0, 2.5, 3.0, 3.5, 4.0, 4.5, 5.0, 5.5, 6.5, 8.0, 10.0 and 15.0 μM final lithium concentrations respectively. As shown in FIG. 1, it is clear that there is a very large enhancement in the fluorescence upon exposure to lithium. Comparing areas of spectra, as calculated over a fixed interval, shows that there is about a 106 fold increase in the fluorescent quantum yield and represents a very high signal to noise ratio.

Figure 2:
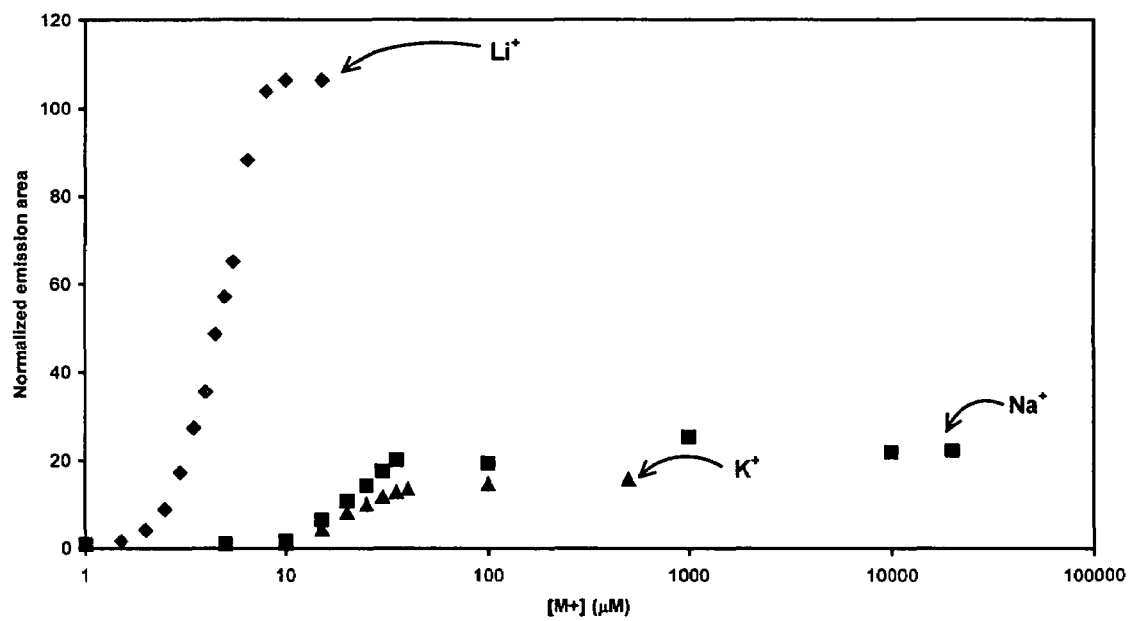
FIG. 2 shows a normalized fluorescence emission area verse the metal cation concentration (M$^+$) of lithium, sodium and potassium.

FIG. 2 shows the normalized fluorescence emission area verse the metal cation concentration ($M^+$) of lithium, sodium, and potassium. The selectivity was calculated based on a previously reported method (Benco, J. S., Nienaber, H. A., Dennen, K., McGimpsey, W. G., *J. Photochem. Photobio. A* 2002, 152, 33). Using the afore-mentioned method, the title compound has a selectivity of at least $logK_{Li,Na} < -3.8$. This value represents the testable limit due to lack of solubility of the sodium salt in the organic media and is likely to be at least an order of magnitude better. Such improved selectivity over the current state of the art is particularly advantageous when the measurement of lithium in biological samples, such as plasma or blood, is concerned where the sodium level is on the order of about 140 mM. At this level a selectivity ratio of about –4.0 is required, as such the title compound of the present invention would be ideally suited. The selectivity of the title compound of the present invention over that of potassium is at least about $logK_{Li,Na} < -2.2$. This again is limited only by the solubility of salt used in the experiment. Based on the known size fit effect and the fact that FIG. 2 shows potassium responding less than sodium it is likely that the true lithium/potassium selectivity is about at least $< -4.0$. In biological samples, the required selectivity for lithium over that of potassium is about –3.0. Consequently, adequate selectivity is provided by the present invention. In conclusion, the presented data demonstrates that the title compound of the present invention is a suitable fluorophore for the selective determination of lithium.

Those skilled in the art will recognize that the preferred embodiment could be modified through organic synthetic techniques to yield a compound suitable for use in ion selective electrodes. This would provide a lithium ion selective electrode with very high selectivity. Specifically, one could form the invention to contain an oxygen moiety at the X site and thus the calixarene moiety will possess an ether crown-3 bridge. The molecule could then be doped into an ion selective matrix and incorporated into an ion selective electrode. Such an ion selective electrode is within the spirit and scope of the present invention.

The present invention also provides a lithium ion sensor, referred to as an "optode" or "optrode", which includes the fluoroionophore of the invention and a transparent support material in which the ionophore is situated (see, for comparison, Buhlmann P et al., Chem Rev. 98: 1593–1687 (1998)). A material is "transparent" for the purposes of this invention if the material is substantially transparent to the wavelength of light that excites the fluoroionophore and the wavelength of light that is emitted from the fluoroionophore, where the excitation wavelength and the emission wavelength are the wavelengths relevant to the actual measurement. For example, the emission from the fluoroionophore can be measured by spectrofluorimetry, a technique that is well known to those of skill in the art. Spectrofluorimeters are commercially available, for example from Perkin Elmer (Shelton, Conn., USA). The excitation and emission spectra of the fluoroionophore can be estimated by one of skill in the art based upon published excitation and emission spectra for the fluorophore and for similar fluorophores.

Under the appropriate conditions, the use of optode of the invention advantageously provides continuous measurement of lithium ion activity in situ and in real-time.

In one embodiment, the fluoroionophore of the present invention is retained in a plasticized poly(vinyl chloride) ("PVC") film as the support material. In a further embodiment of the present invention, the film is placed on the end of an optically conductive fiber ("an optic fiber bundle"). The optic fiber bundle can be connected directly to a spectrofluorimeter for ease of measurement. Commercially obtainable optic fiber bundles may be used.

In other embodiments of the present invention, the support material is a material selected from PVC, Nafion and sol-gel materials such as silicate or mixtures such as polyvinylformal-silica (see, Flamini & Panusa, Sens. Actuators, B42: 39 (1997)).

In one embodiment, the compound of the invention is covalently immobilized to the support material through attachment to the ionophore through the R groups or to the fluorophore (see, U.S. Pat. No. 6,294,390).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:
1. A compound, having the structure:

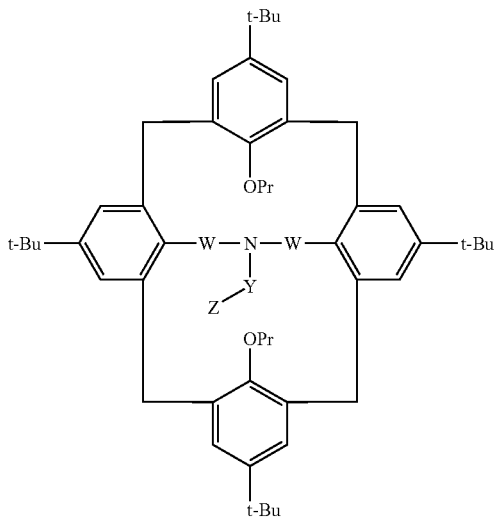

wherein,
(a) W is —O(CH$_2$)$_2$—;
(b) Y is —CH$_2$—; and
(c) Z is a fluorophore;
wherein the compound selectively binds lithium ions as compared to potassium and/or sodium ions.

2. The compound of claim 1 wherein the fluorophore is anthracene.

3. The compound of claim 1 wherein Z is selected so that a negative, thermo-neutral or slightly positive free energy value is obtained from the Rehm-Weller equation for the compound.

4. A device for the detection of lithium ions, comprising:
a compound according to claim 1
a support material,
wherein the compound is engaged to the support material.

5. The device of claim 4, wherein Z is selected so that a negative, thermo-neutral or slightly positive free energy value is obtained from the Rehm-Weller equation for the compound.

6. The device of claim 4, wherein the presence of Z in the compound allows for optical detection either through modulation of absorption and/or fluorescence.

7. The device of claim 4, wherein the Z is anthracene.

8. The device of claim 4, wherein the support material is a transparent support material.

9. The device of claim 4 wherein the support material is Nafion.

10. The device of claim 4 wherein the support material is a sol gel material.

11. The device of claim 10 wherein the sol gel material is silicate.

12. The device of claim 10 wherein the sol gel material is polyvinylformal-silica.

13. The device of claim 4 wherein the support material is a plasticized poly(vinyl chloride) film.

14. The device of claim 13 wherein the plasticized poly (vinyl chloride) film is placed on an end of an optically conductive fiber.

15. The device of claim 14 wherein the optically conductive fiber is connected directly to a spectrofluorimeter.

16. A method of determining lithium ion concentration of a biological fluid, comprising:
(i) providing a device comprising a compound according to claim 1;
(ii) placing the device into the biological fluid; and
(iii) measuring a signal, wherein the signal indicates a lithium ion concentration of the biological fluid.

17. The method of claim 16 wherein the device is an optical sensor.

18. The method of claim 16 wherein the device is an ion selective electrode.

19. The method of claim 16 wherein the signal is a fluorescence.

20. The method of claim 16 wherein the biological fluid is whole blood.

21. The method of claim 16 wherein the biological fluid is serum.

22. The method of claim 16 wherein the biological fluid is plasma.

23. The method of claim 16 wherein the biological fluid is cerebrospinal fluid.

24. The method of claim 16 wherein the biological fluid is urine.

25. The method of claim 16 wherein the biological fluid is amniotic fluid.

26. The method of claim 16 wherein the biological fluid is saliva.

27. The method of claim 16 wherein the biological fluid is tears.

28. The method of claim 16 wherein Z is anthracene.

29. The method of claim 16 wherein Z is selected so that a negative, thermo-neutral or slightly positive free energy value is obtained from the Rehm-Weller equation for the compound.

* * * * *